(12) United States Patent
Lu

(10) Patent No.: US 9,962,248 B2
(45) Date of Patent: May 8, 2018

(54) DENTAL FLOSSING APPARATUS

(71) Applicant: Peng Lu, Sunnyvale, CA (US)

(72) Inventor: Peng Lu, Sunnyvale, CA (US)

(*) Notice: Subject to any disclaimer, the term of this patent is extended or adjusted under 35 U.S.C. 154(b) by 169 days.

(21) Appl. No.: 14/771,124

(22) PCT Filed: Apr. 27, 2015

(86) PCT No.: PCT/US2015/027838
§ 371 (c)(1),
(2) Date: Aug. 27, 2015

(87) PCT Pub. No.: WO2015/179070
PCT Pub. Date: Nov. 26, 2015

(65) Prior Publication Data
US 2016/0361148 A1    Dec. 15, 2016

Related U.S. Application Data

(60) Provisional application No. 61/994,896, filed on May 18, 2014.

(51) Int. Cl.
*A61C 15/00* (2006.01)
*A61C 15/04* (2006.01)

(52) U.S. Cl.
CPC ................. *A61C 15/046* (2013.01)

(58) Field of Classification Search
CPC ........ A61C 15/00; A61C 15/04; A61C 15/046
See application file for complete search history.

(56) References Cited

U.S. PATENT DOCUMENTS

| | | | |
|---|---|---|---|
| 1,468,942 | A | 9/1923 | Gamble |
| 1,700,690 | A | 1/1929 | Stafford |
| 3,759,272 | A | 9/1973 | Di Vincenti |
| 3,915,178 | A | 10/1975 | Zellers |
| 4,031,909 | A | 6/1977 | Kelley |
| 4,254,786 | A | 3/1981 | Won |
| 5,201,330 | A | 4/1993 | Won |
| 5,217,031 | A | 6/1993 | Santoro |
| 5,417,232 | A | 5/1995 | Ballard |

(Continued)

OTHER PUBLICATIONS

Lu, Peng, International Search Report and Written Opinion, PCT/US2015/027838, dated Jul. 24, 2015, 7 pgs.

(Continued)

*Primary Examiner* — Rachel Steitz
(74) *Attorney, Agent, or Firm* — Morgan, Lewis & Bockius LLP

(57) ABSTRACT

A flossing device includes a housing that can be gripped as a handle. The housing has a hollow interior with first pawl teeth. A spool is placed inside the hollow interior and includes second and third pawl teeth disposed on opposite ends. The second pawl teeth, when engaged with the first pawl teeth with assistance from a spring, allow the spool to rotate in a first direction relative to the housing. The flossing device also includes a tail cap that has fourth teeth that engage the third pawl teeth to urge the spool in the first direction. The flossing device also includes a fork for suspending a length of floss received from the spool and used for flossing. The length of floss is tightened by rotation of the spool in the first direction. The length of floss can be replaced by rotation of the spool in a second direction opposite the first direction.

18 Claims, 11 Drawing Sheets

(56) References Cited

U.S. PATENT DOCUMENTS

| | | | |
|---|---|---|---|
| 5,657,780 | A | 8/1997 | Giacopuzzi |
| 5,823,207 | A | 10/1998 | Bushman |
| 7,156,110 | B2 | 1/2007 | Landry |
| 7,201,173 | B2 | 4/2007 | Shen et al. |
| 7,305,997 | B2 | 12/2007 | Liu et al. |
| 2004/0163665 | A1 | 8/2004 | Alvarez |
| 2005/0092347 | A1 | 5/2005 | Fan |
| 2006/0254610 | A1* | 11/2006 | Chen .................. A61C 15/046 132/325 |
| 2006/0260637 | A1 | 11/2006 | Kossak et al. |
| 2007/0204879 | A1 | 9/2007 | Chen et al. |
| 2008/0289648 | A1 | 11/2008 | Liu |
| 2010/0006120 | A1 | 1/2010 | Shen et al. |
| 2011/0284023 | A1 | 11/2011 | Borg et al. |

OTHER PUBLICATIONS

Lu, International Preliminary Report on Patentability, PCT/US2015/027838, dated Nov. 22, 2016, 5 pgs.

* cited by examiner

DENTAL FLOSSING APPARATUS

CROSS REFERENCE TO RELATED APPLICATIONS

This Application is a United States National Stage Application filed under 35 U.S.C. § 371 of PCT Patent Application Serial No. PCT/US2015/027838 filed on Apr. 27, 2015, which claims the benefit of and priority to U.S. Patent Application No. 61/994,896 filed on May 18, 2014, which is hereby incorporated by reference in its entirety.

TECHNICAL FIELD

The disclosed embodiments relate to reusable devices for dental flossing.

BACKGROUND

Flossing can help reduce both tooth cavities and gum diseases. Therefore, dentists suggest that people floss their teeth every day. To do so, some people stretch a strand of floss between two fingers and put their fingers into their mouth. Because it is hard to hold the floss in the limited space of the mouth, this method is not convenient. Alternatively, some people use disposable floss holders, e.g., a strand (or length) of floss attached between two plastic prongs that is discarded after use. These disposable floss holders can be used only once and therefore create unnecessary waste and pollution. There is a need for a versatile and easy-to-operate flossing device.

SUMMARY

A flossing device is provided that includes a housing forming a handle of the flossing device. The housing has a hollow interior with a first set of one or more pawl teeth disposed within the hollow interior. The flossing device also includes a spool, disposed within the hollow interior of the housing, for holding floss. The spool includes a second set of one or more pawl teeth disposed on a first end of the spool and a third set of one or more pawl teeth disposed on a second end of the spool opposite the first end of the spool. The second set of one or more pawl teeth, when engaged with the first set of one or more pawl teeth, allows the spool to rotate in a first direction relative to the housing. The flossing device has a tail cap that includes a fourth set of one or more pawl teeth that engages the third set of one or more pawl teeth to urge the spool in the first direction. The flossing device further includes a fork for suspending a length of floss received from the spool. The length of floss is used for flossing by a user of the flossing device. Further, the length of floss is tightened by rotation of the spool in the first direction and dispensed by rotation of the spool in a second direction opposite the first direction.

In some embodiments, the flossing device further includes a spring disposed between the spool and the tail cap.

In some embodiments, the tail cap is configured to be positioned in a plurality of positions including a first position where compression of the spring exerts a force on the spool to cause engagement of the second set of one or more pawl teeth with the first set of one or more pawl teeth and a second position where the spring does not cause restrictive engagement of the first set of one or more pawl teeth with the second set of one or more pawl teeth.

In some embodiments, the fourth set of one or more pawl teeth drives the third set of one or more pawl teeth when the tail cap is in the first position.

In some embodiments, the fourth set of one or more pawl teeth disengages with the third set of one or more pawl teeth when the tail cap is in the second position.

In some embodiments, the tail cap is mechanically coupled with the spool such that the second set of one or more pawl teeth is disengaged from the first set of one or more pawl teeth when the tail cap is in the second position.

In some embodiments, when the tail cap is in the second position, the spool is rotatable in a second direction opposite the first direction. The length of floss is loosened or dispensed by rotation of the spool in the second direction.

In some embodiments, the tail cap is coupled with the housing using a threaded connection. The tail cap is in the first position when the tail cap is screwed toward the housing using the threaded connection and the tail cap is in the second position when the tail cap is loosened using the threaded connection beyond a mechanical threshold that disengages the second set of one or more pawl teeth from the first set of one or more pawl teeth.

In some embodiments, the tail cap is capable of rotating freely in the first direction when the tail cap is in the first position.

In some embodiments, the length of floss is replaced across the fork with a fresh length of floss by the user pulling on the floss with the tail cap in the second position, thereby dispensing the fresh length of floss from the spool.

In some embodiments, the housing includes an assembly of separately manufactured components.

In some embodiments, the flossing device further includes a releasable clamp for clamping a loose end of the floss in order to maintain tension in the length of floss suspended by the fork.

In some embodiments, the flossing device further includes a support bar coupling the fork with the housing. The support bar includes a thread and the releasable clamp includes a screw nut positioned around the support bar to be tightened against the thread.

In some embodiments, the flossing device is a reusable handheld flossing device.

In some embodiments, the spool is reloadable by the user.

In some embodiments, the spool is not reloadable by the user.

In some embodiments, the flossing device further includes an apparatus (e.g., a pulley system) for dispensing the floss from the spool. The apparatus includes a movable slider having a hole. The floss is threaded through the hole such that, when an end of the floss is pulled to release additional floss from the spool, the floss exerts a first force on the movable slider in a first direction substantially along an axis of the spool. The apparatus further includes an elastic object coupled with the movable slider that exerts a second force on the movable slider in an opposite direction to the first direction when the elastic object is stretched.

In some embodiments, the apparatus further includes a moving block coupled with the elastic object. The moving block is displaced by changes in a tension of the elastic object. The apparatus further includes a cable coupled with the moving block and the moveable slider. The apparatus further includes a fixed block that is fixed in position with respect to the spool. The fixed block has a plurality of threading holes through which to thread the cable. The cable is threaded through the plurality of threading holes of the fixed block so as to change the direction of the cable.

BRIEF DESCRIPTION OF THE DRAWINGS

Like reference numerals refer to corresponding parts throughout the drawings.

DETAILED DESCRIPTION OF EMBODIMENTS

Reference will now be made in detail to various implementations, examples of which are illustrated in the accompanying drawings. In the following detailed description, numerous specific details are set forth in order to provide a thorough understanding of the present disclosure and the described implementations herein. However, implementations described herein may be practiced without these specific details. In other instances, well-known methods, procedures, components, and mechanical apparatus have not been described in detail so as not to unnecessarily obscure aspects of the implementations.

In accordance with some embodiments, a flossing device is used for holding a section or length of dental floss (sometimes referred to herein as "floss") in order to remove foreign substances lodged between a user's teeth. Accordingly, the embodiments of the present disclosure provide several advantages:

the flossing device described herein tightens and releases the dental floss easily;

the amount of tension applied to the dental floss can be adjusted conveniently;

the flossing device allows the tensioned dental floss to comfortably reach hard-to-reach back teeth;

dirty dental floss can be removed immediately after use and replaced with new dental floss;

the amount (e.g., length) of the dental floss for each use is reduced;

the amount of dental floss exposed outside of the flossing device is reduced, promoting hygiene; and in some embodiments, the floss is reloadable after a certain amount (e.g. a spool cartridge, or a predefined amount) has been used.

Other advantages of the present disclosure will be apparent from a consideration of the drawings and ensuing description.

Figure 1:
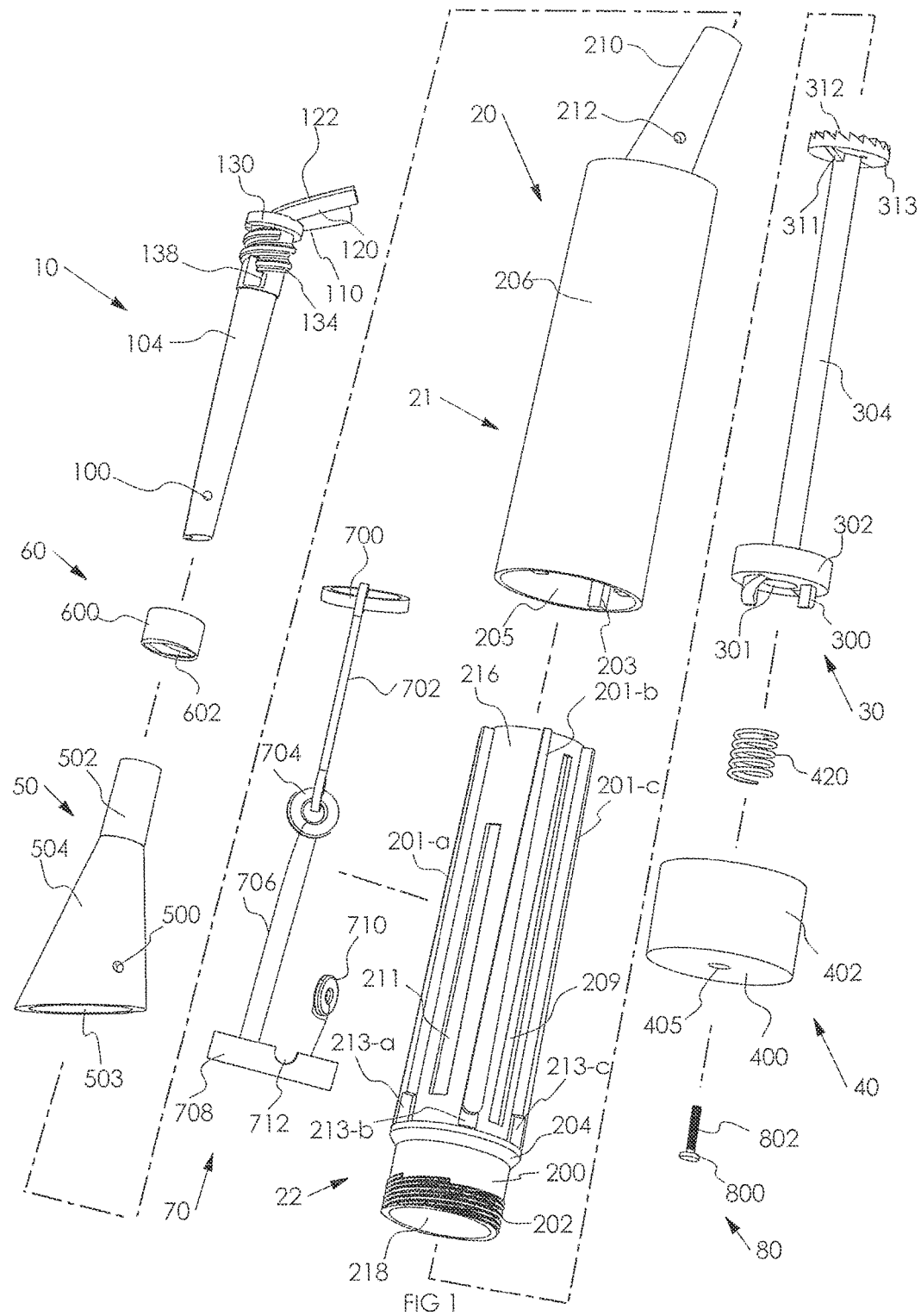
FIG. 1 is an exploded perspective view of a flossing device, in accordance with some embodiments.
Figure 2:
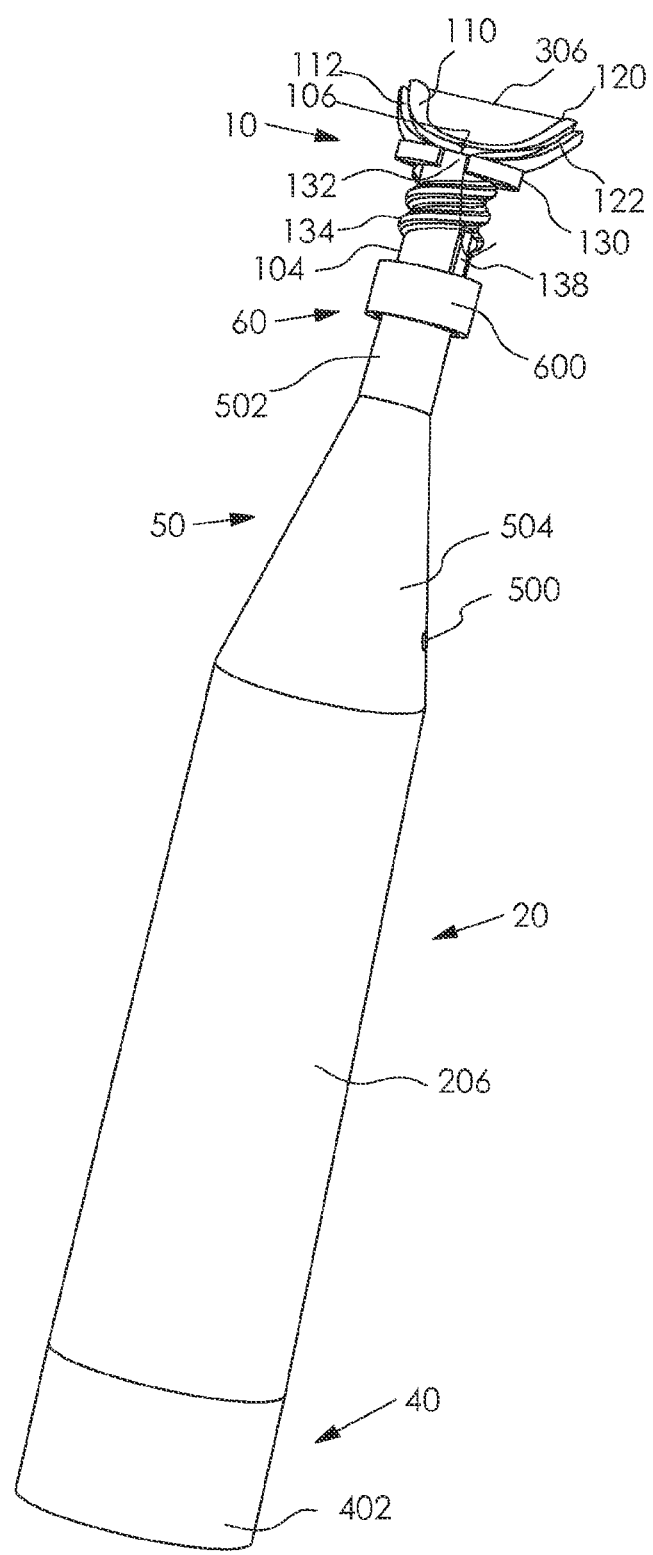
FIG. 2 is a perspective view of the assembled flossing device, in accordance with some embodiments.

With reference to FIGS. 1 and 2, some embodiments provide a flossing device for tightening, releasing, and cutting a string of dental floss. In some embodiments, the flossing device is a reusable handheld flossing device, meaning that the flossing device is intended to be used to floss on more than one occasion. For example, in some embodiments, the flossing device is reusable until a preloaded amount of floss has been used, at which point the flossing device is disposed of. Alternatively, in some embodiments, the flossing device is reusable and refillable, meaning that once a preloaded amount of floss has been used, the user can add more floss (e.g., by replacing the used spool cartridge with a new spool cartridge as described below).

The flossing device, in accordance with some embodiments, comprises a head 10, a clamping nut 60, a cover 50, a main body 20 (sometimes referred to herein as "housing"), a pulley system 70, a spool 30, a tail cap 40, and a screw 80. FIG. 2 shows the flossing device assembled for use. The head 10 is securely mounted on top of the main body 20, where the lower part of the head 10 is enclosed by the cover 50. In some embodiments, when the clamping nut 60 is not secured to the support bar (as described below), the clamping nut 60 rests around the cover 50. The floss spool 30 (sometimes referred to herein as "the spool") is placed inside the main body 20 and the tail cap 40 is screwed on the main body 20 at the bottom.

Figure 3:
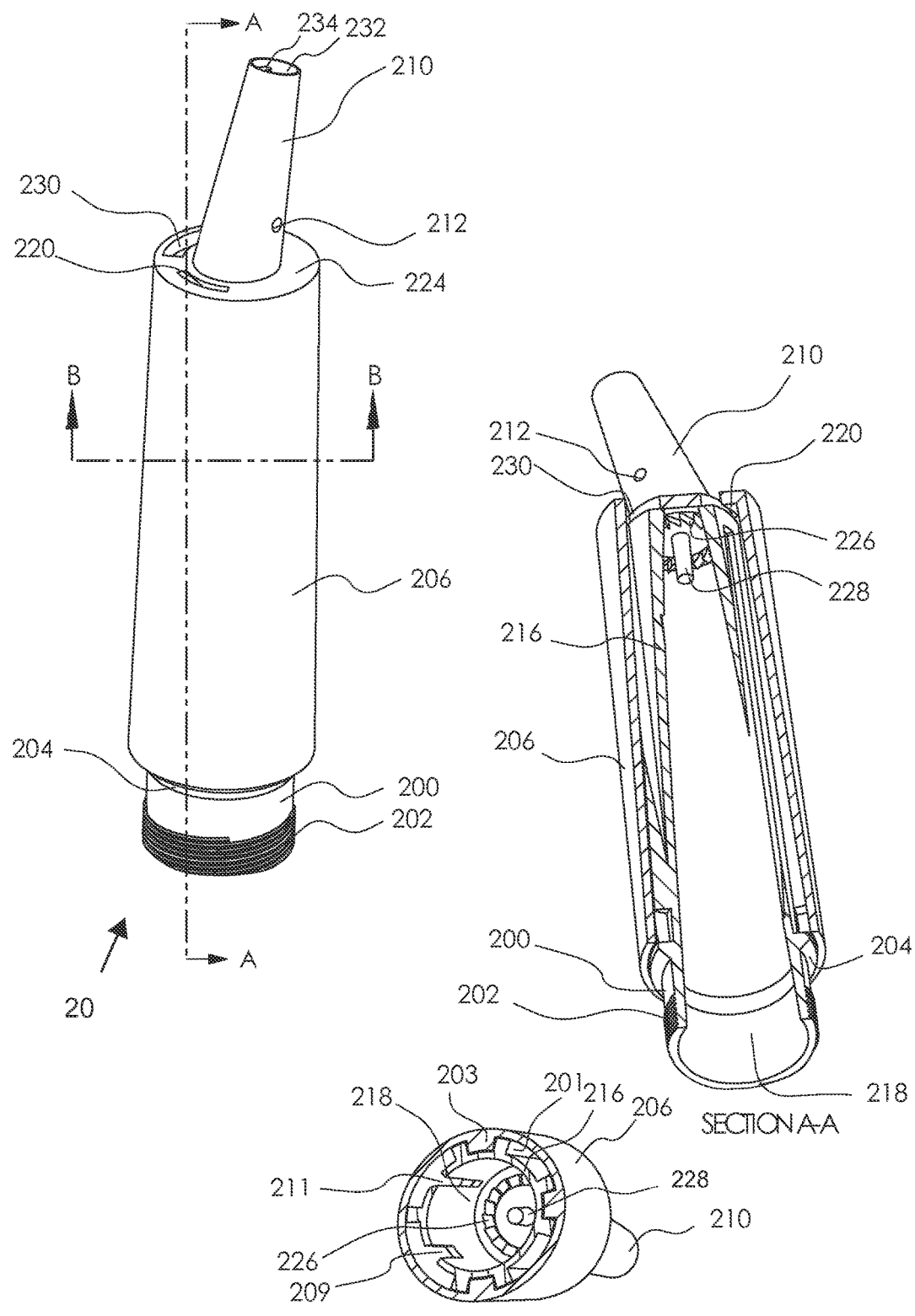
FIG. 3 is a perspective sectional view of a main body of the flossing device, in accordance with some embodiments.
Figure 4:
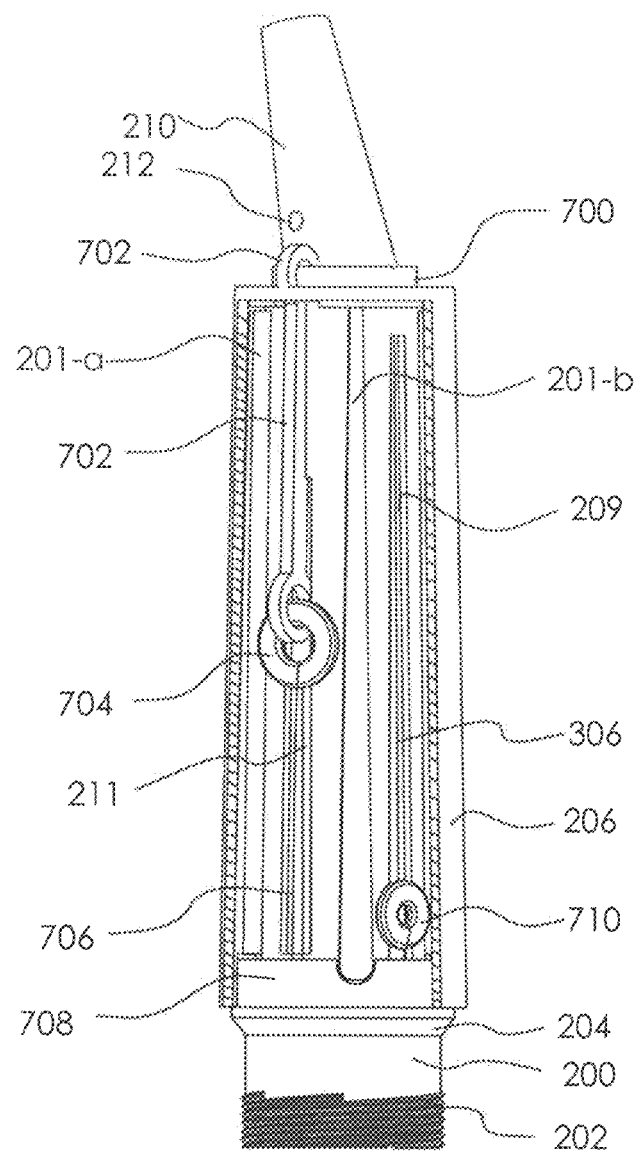
FIG. 4 is a break-out view showing a pulley system within the main body of the flossing device, in accordance with some embodiments.

With reference to FIGS. 1, 3 and 4, the main body 20 (e.g., the housing) comprises an upper body part 21 and a lower body part 22. That is to say, in some embodiments, the housing includes an assembly of separately manufactured components. In some embodiments, the housing forms a handle of the flossing device (e.g., in use, the user wraps her fingers around the housing to grasp the flossing device). In some embodiments, the housing has a hollow interior (e.g., defined by the hollow interior of the lower body part 22). In some embodiments, the upper body part 21 of the housing has a tubular outer wall 206, one or more inner ribs 203, a lower-body receiving chamber 205, a support base 224, a band opening 230, an threading opening 220, one or more first body-pawl teeth 226, an axle 228, a head mounting section 210, a head receiving chamber 232, an installation rib 234, and a head mounting hole 212.

In some embodiments, the one or more first body-pawl teeth 226 constitute a first set of one or more pawl teeth. In some embodiments, the first set of one or more pawl teeth includes a single pawl tooth. Alternatively, in some embodiments, the first set of one or more pawl teeth includes a plurality of pawl teeth. In some embodiments, the first set of one or more pawl teeth are disposed within the hollow interior. For example, in some embodiments, the first set of one or more pawl teeth are rigidly formed into or attached to the interior of the upper body part 21 (as shown in more detail with reference to FIG. 3).

With reference to FIGS. 1 and 3, in some embodiments, the inner ribs 203 are formed longitudinally on the inner surface of the outer wall 206. The lower-body receiving chamber 205 is defined by the outer wall 206. The support base 224 is circular and is securely mounted on top of the outer wall 206, with the first body-pawl teeth 226 formed on its lower surface. The pawl teeth are unidirectional in nature, that is, each pawl tooth has a stop face and a deflection face. The threading opening 220 and band opening 230 are defined by the support base 224. The axle 228 is a column protruding from the lower surface of the support base 224 at the center for supporting the spool 30 when it is being rotated. The head mounting section 210 is tubular and protrudes upwardly from the upper surface of the support base 224 at an angle and is inwardly tapered as it extends. The head receiving chamber 232 is defined by the head mounting section 210. The installation rib 234 is defined by the inner surface of the head mounting section 210 for fixing the head 10 when it is inserted into the head receiving chamber 232. The head mounting hole 212 is defined on the head mounting section 210 for mounting the cover 50 and the head 10.

In some embodiments, the lower body part 22 has a tubular inner wall 216, one or more outer ribs 201 (e.g., outer rib 201-*a*; 201-*b*; and 201-*c*), a spool receiving chamber 218, a free rotation section 200, a body threaded section 202, a body tapered section 204, a moving block guiding groove 211, a slider guiding groove 209, and fixing notches 213 (e.g., fixing notch 213-*a*; 213-*b*; and 213-*c*). The moving block guiding groove 211 and slider guiding groove 209 are defined by the inner wall 216. The outer ribs 201 are formed longitudinally on the outer surface of the inner wall 216. The fixing notches 213 are formed by cutting out portions of the bottoms of the outer ribs 201. The body tapered section 204 is at the bottom of the inner wall 216 and connects the inner wall 216 to the tubular free rotation section 200, which is unthreaded. The tubular body threaded section 202 extends from the free rotation section 200. The spool receiving chamber 218 is defined by the inner wall 216, the body tapered section 204, the free rotation section 200, and the body threaded section 202. In some embodiments, the spool 30 is disposed (e.g., positioned and/or placed) within the spool receiving chamber 218 (e.g., the spool 30 is disposed within the hollow interior of the housing).

The spool 30 holds dental floss that is wrapped around the spool 30. In some embodiments, the spool 30 is reloadable by the user. This is performed in a number of different ways, in accordance with a variety of embodiments. For example, in some embodiments, the user can remove the spool 30, wrap fresh dental floss around (e.g., directly around) the spool 30, and re-thread the floss as described below. Alternatively, in some embodiments, the spool 30 receives a reloadable spool cartridge that fits snuggly and/or tightly over the spool 30 (that is to say, when the spool 30 is rotated as described herein, the spool cartridge rotates together with the spool 30). In some embodiments, the floss is not directly wound onto the spool, but is wound onto a spool cartridge that is coupled with the spool. In some embodiments, the spool is not reloadable by the user (e.g., the flossing device is disposable once a pre-loaded amount of dental floss has been used).

The main body/housing 20 is formed by inserting the lower body part 22 into the lower-body receiving chamber 205 until the top of the inner wall 216 reaches the support base 224 (e.g. the lower surface of the support base 224). In some embodiments, the inner ribs 203 and the outer ribs 201 are mechanically complementary. Namely, the inner ribs 203 lock the outer ribs 201 to prevent the lower body part 22 from rotating relative to the upper body part 21. In some embodiments, the lower body part 22 and the upper body part 21 are assembled in a press-fit manner to prevent the lower body part 22 from sliding out of the upper body part 21. The first body-pawl teeth 226 (comprising the first set of one or more pawl teeth) are enclosed by the inner wall 216. The moving block guiding groove 211 communicates with the band opening 230 and the slider guiding groove 209 communicates with the threading opening 220.

Figure 10:
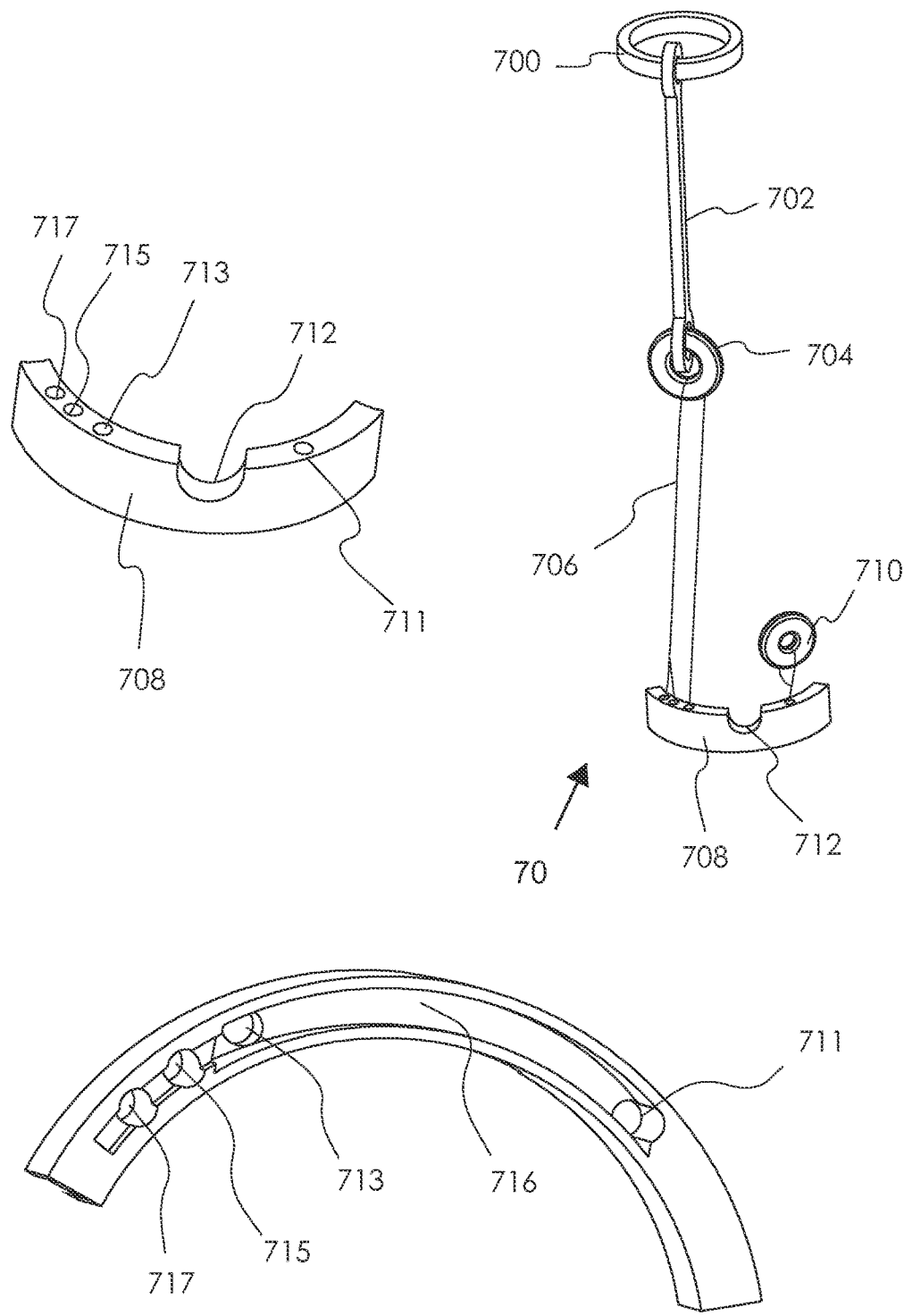
FIG. 10 is a perspective view of the pulley system of the flossing device and an enlarged view of a fixed block component of the pulley system, in accordance with some embodiments.

With reference to FIGS. 1, 4 and 10, in some embodiments, the pulley system includes a mounting ring 700, an elastic band 702, a moving block 704, a cable 706, a fixed block 708, and a slider 710 (e.g., a movable slider). The mounting ring 700 is placed around the head mounting section 210. Elastic band 702 is an example of an elastic object. Another example of an elastic object is a spring. The moving block 704 and the slider 710 are ring-shaped (e.g., the moving block 704 and the slider 710 each has a hole through which floss or cable may be threaded). The fixed block 708 is fixed in position with respect to the spool 30. The fixed block 708 has a plurality of threading holes through which to thread the cable 706 including: fixing holes 715 and 717 and direction-changing holes 713 and 711. The fixed block 708 has a direction-changing groove 716, and an installation notch 712 that matches the fixing notch 213-*b*. The mounting ring 700 is securely mounted around the head mounting section 210 without blocking the threading opening 220 and the band opening 230. One end of the elastic band 702 is fixed to the mounting ring 700 and the other end goes through the band opening 230 and is fixed to the moving block 704. The moving block 704 is placed in a chamber created by the inner wall 216, outer wall 206, and outer ribs 201-*a* and 210-*b*. The slider 710 is placed in a chamber created by the inner wall 216, outer wall 206, and outer ribs 201-*b* and 210-*c*. The fixed block 708 is mounted on the fixing notches 213 with the installation notch 712 matching the fixing notch 213-*b*. The fixed block 708 is locked in the fixing notches 213 when the lower body part 22 is inserted in to the upper body part 21. One end of the cable 706 is fixed to the fixed block 708 via the fixing holes 715 and 717. The other end is threaded firstly through the hole in the moving block 704 for engaging the elastic band 702 with the slider 710. The other end of the cable 706 is further threaded through the fixed block 708 by sequentially threading through the direction-changing hole 713, the direction-changing groove 716 and the direction-changing hole 711 for changing the direction of force. Finally, the other end of the cable 706 is attached to the slider 710.

When the slider 710 is pulled upwardly, due to the force propagated through the cable 706 to the moving block 704, the elastic band 702 is stretched allowing the slider 710 to move up. At the same time, the stretched elastic band 702 also exerts a downward force on the slider 710, strength of which increases when the elastic band 702 is extended longer. As a result, the slider 710 moves up along the slider guiding groove 209 to a position where the upward force exerted on the slider 710 and the downward force from the elastic band 702 are balanced. When no force is exerted on the slider 710, the elastic band 702 retracts and pulls the slider 710 toward the fixed block 708, which is disposed at the bottom of the slider guiding groove 209.

Figure 5:
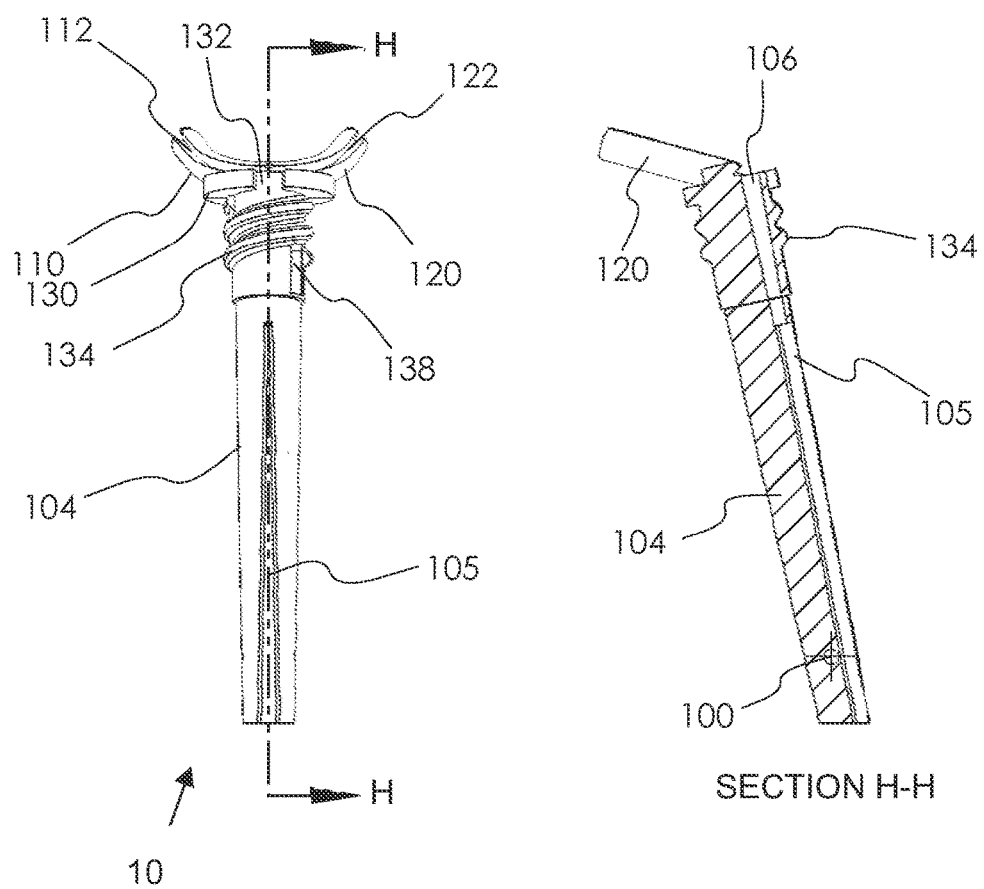
FIG. 5 is a sectional view of a head of the flossing device, in accordance with some embodiments.

With reference to FIGS. 1, 2, and 5, the head 10 comprises an assembly hole 100, a support bar 104, an installation slot 105, a head thread section 134, a fastening notch 138, a bolt head 130, a threading notch 132, a first arm 110, a first-arm guiding groove 112, a second arm 120, a second-arm guiding groove 122, and a threading hole 106. The first arm 110 and the second arm 120 constitute a fork (also called a yoke). The fork (e.g. yoke) suspends a length of floss received from the spool 30 that is used for flossing by a user of the flossing device. The installation slot 105 is along the support bar 104 and connects to the threading hole 106. The support bar 104 can be inserted into the head receiving chamber 232, with the installation slot 105 matching the installation rib 234.

In some embodiments, the flossing device includes a releasable clamp for clamping a loose end of the floss in order to maintain tension in the length of floss suspended by the fork. In some embodiments, the releasable clamp is positioned on the support bar 104, which couples the fork with the housing. In some embodiments, the support bar 104 includes a thread (e.g., head thread section 134) and the releasable clamp includes a clamping nut (e.g., clamping nut 60) positioned around the support bar 104 to be tightened against the thread (thus fastening the thread).

The bolt head 130 is oval-shaped and is disposed on top of the head thread section 134 at the joint of the first arm 110 and second arm 120. The threading hole 106 extends from the top of the bolt head 130 to the installation slot 105 for threading the floss. The arms 110, 120 are intended to support a usable length of dental floss between them to floss teeth. The first arm 110 extends outwardly from one side of the support bar 104 at its distal end. The first-arm guiding groove 112 is formed on the outer surface of the first arm 110 and is connected to the threading hole 106 to guide the floss along the first arm 110. The second arm 120 extends outwardly from the opposing side of the support bar 104 to the first arm 110. The second-arm guiding groove 122 is formed on the outer surface of the second arm 120 for guiding the floss along the second arm 120 downwardly to the head thread section 134. The threading notch 132 further leads the floss toward the fastening notch 138 so that its distal end is fastenable to the head thread section 134, as described below. The first arm 110 and the second arm 120 are spaced apart from the support bar 104 to form a U-shaped fork. The fork is oriented at a predetermined angle from the support bar 104. In some embodiments, the predetermined angle is about 120 degrees to allow for an easy flossing operation. The support bar 104 protrudes from the head thread section 134 for extending the fork into the mouth when flossing. The installation slot 105 is defined on the outer surface of the support bar 104, which is mated with the installation rib 234 for locking the head 10 when it is inserted into the head receiving chamber 232.

Figure 8:
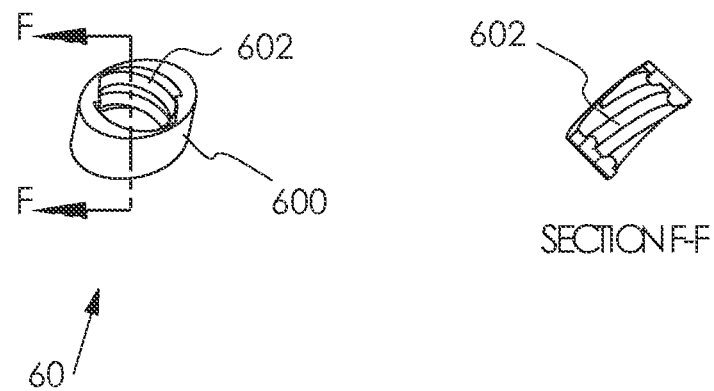
FIG. 8 is a sectional view of a clamping nut of the flossing device, in accordance with some embodiments.

With reference to FIGS. 1, 2 and 8, the clamping nut 60 is rotationally mounted around the support bar 104 and is to be used in conjunction with the head thread section 134 to form the releasable clamp. The clamping nut 60 includes a nut body 600, and a nut screw thread 602. The outer surface of the nut body 600 corresponds to the outer surface of the bolt head 130. The nut screw thread 602 is formed on the inner surface of the nut body 600. The nut screw thread 602 corresponds to and engages the head thread section 134. When the clamping nut 60 is screwed onto the head thread section 134, friction is created to pinch and fasten the distal end of the floss.

Figure 7:
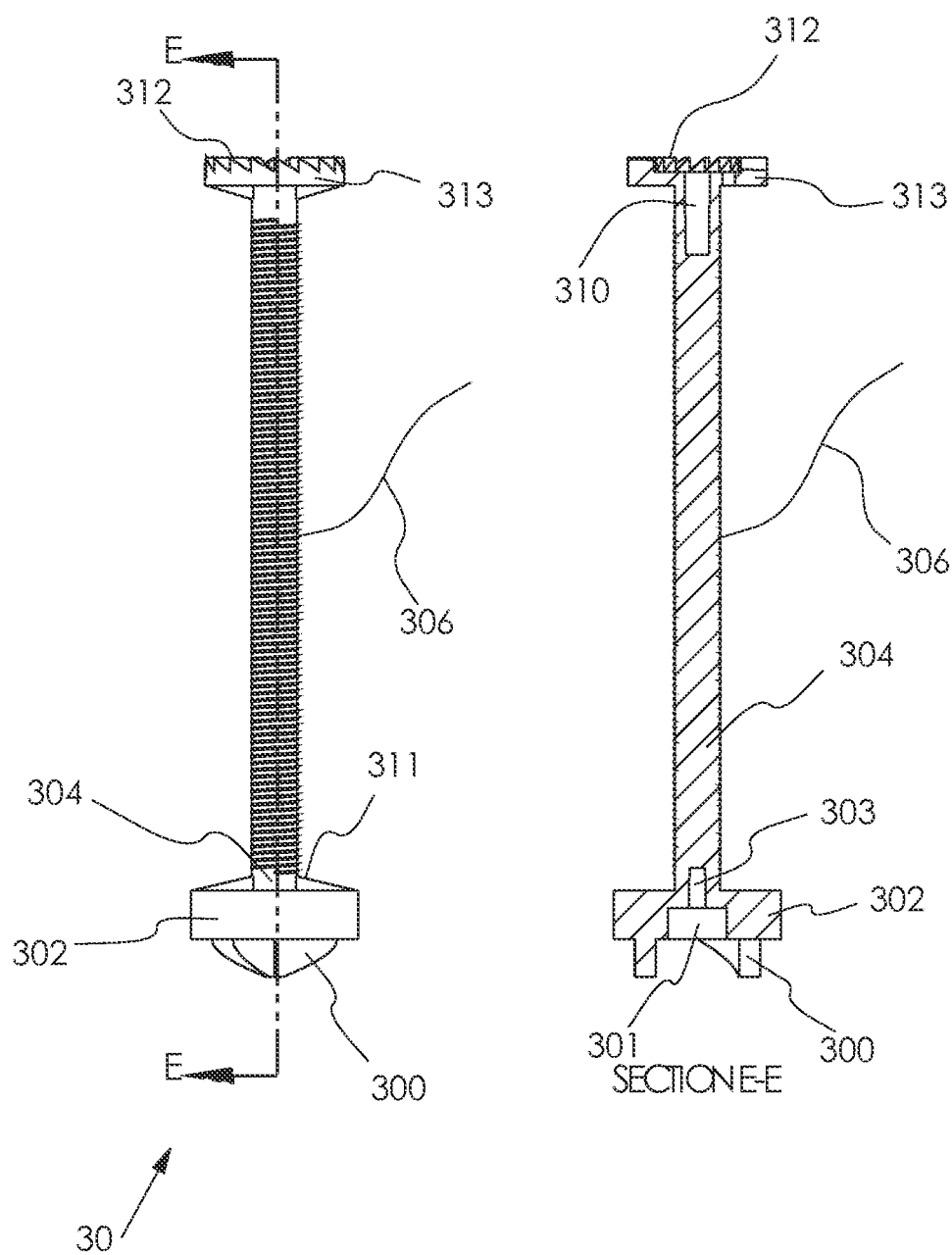
FIG. 7 is a sectional view of a spool of the flossing device, in accordance with some embodiments.

With reference to FIGS. 1 and 7, the floss spool 30 comprises a reel 304, a main-body head 313, a main-body holding hole 310, one or more second body-pawl teeth 312, a cap head 302, one or more second tail-pawl teeth 300, a tube holding hole 301, a screw receiving hole 303, and ribs 311. The dental floss 306 is wound around the reel 304 (which may be embodied a replaceable spool cartridge).

In some embodiments, the one or more second body-pawl teeth 312 constitute a second set of one or more pawl teeth disposed on a first end of the spool (the first end is the end that is disposed toward support base 224). In various embodiments, the second set of one or more pawl teeth includes a single pawl tooth or a plurality of pawl teeth. In some embodiments, the second set of pawl teeth, when engaged with the first set of pawl teeth, allows the spool to rotate in only a single direction (e.g., a first/tightening direction).

The reel 304 is cylindrical and has a first end and a second end corresponding to the first end and second end of the spool, respectively. The dental floss 306 is wound on the reel 304 in a way such that, when the floss spool 30 is spinning in the tightening direction (e.g. the first direction), the dental floss 306 is wound back on the reel 304 if its distal/free end is not fastened. On the other hand, when the floss spool 30 is spinning in the opposite direction (e.g., a second/unscrewing direction), the dental floss 306 is loosened and can be released by pulling its free end. The main-body head 313 and cap head 302 are enlarged discs formed on the first end and second end of the reel 304, respectively. The main-body holding hole 310 is a blind hole defined at the center of the main-body head 313 and reel 304, which is mated with the axle 228 for holding the spool 30. The second body-pawl teeth 312 are formed on top of the main-body head 313 and are, depending on the position of the tail cap (as explained below), mated/engaged with the first body-pawl teeth 226. The cap head 302 has an annular outer surface and a lower surface. In some embodiments, the spool 30 includes the second tail-pawl teeth 300. In some embodiments, the second tail-pawl teeth 300 are formed on the lower surface of the cap head 302. In some embodiments, the second tail-pawl teeth 300 constitute a third set of one or more pawl teeth disposed on a second end of the spool 30 that is opposite the first end of the spool 30 (e.g., toward tail cap 40). In various embodiments, the second tail-pawl teeth 300 include a single pawl tooth or a plurality of pawl teeth. In some embodiments, the second tail-pawl teeth 300 are evenly positioned around a circle with a gap between two adjacent ones. The tube holding hole 301 is defined at the center of the cap head 302 and the screw receiving hole 303 is a narrower blind hole extending from the tube holding hole 301.

Figure 6:
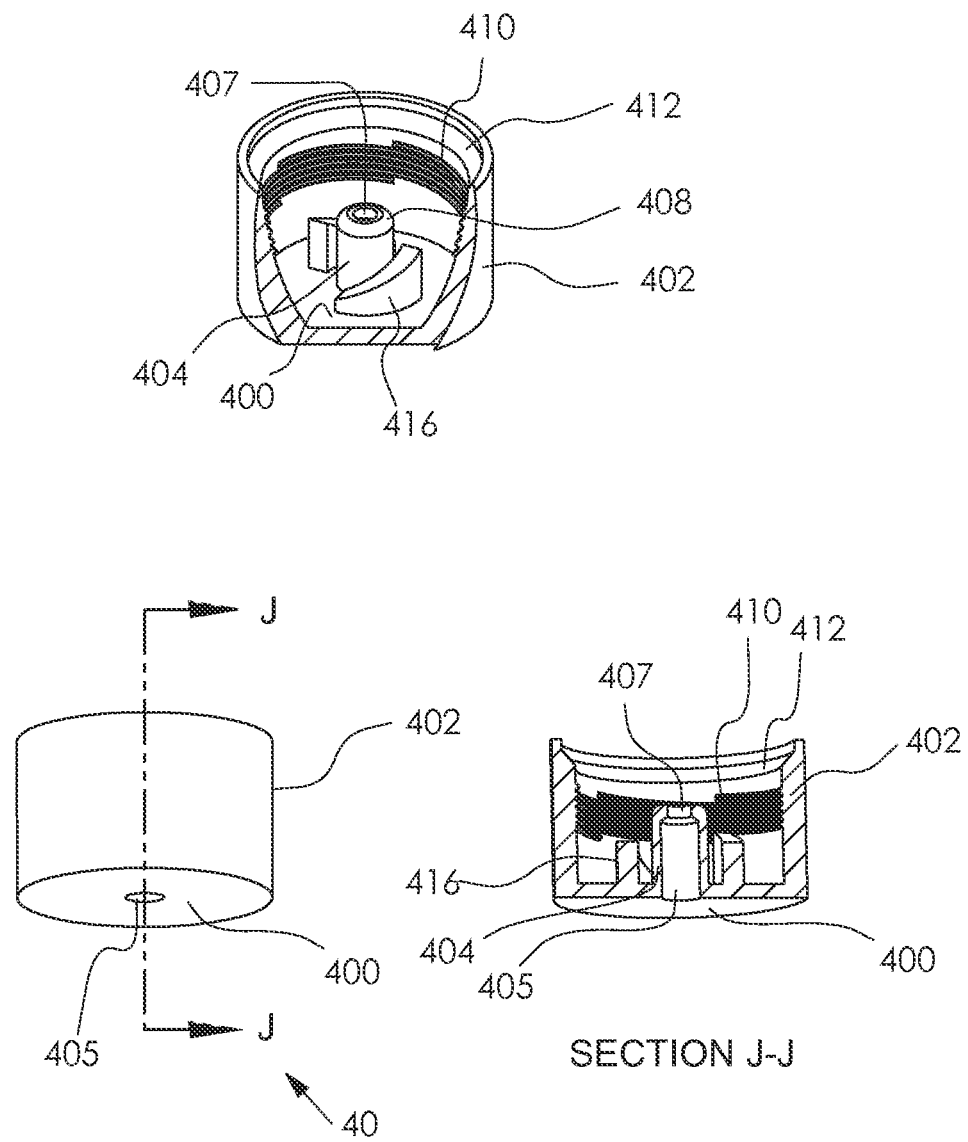
FIG. 6 is a break-out and sectional view of a tail cap of the flossing device, in accordance with some embodiments.

With reference to FIGS. 1 and 6, the tail cap 40 comprises a cap base 400, a cap body 402, a cap wedged section 412, a cap screw thread 410, a tube 404, a tapered section 408, one or more first tail-pawl teeth 416, a screw opening 405, a screw mounting hole 407, and a spring 420.

In some embodiments, the one or more first tail-pawl teeth 416 constitute a fourth set of one or more pawl teeth that engage the third set of one or more pawl teeth. In various embodiments, the fourth set of one or more pawl teeth includes a single pawl tooth or a plurality of pawl teeth. In some embodiments, the fourth set of pawl teeth, when engaged with the third set of pawl teeth, urges the spool 30 in the first direction via rotation of the tail cap 40. In this manner, the length of floss suspended across the fork is tightened.

The cap base 400 is a circular disk with the screw opening 405 at its center. The cap body 402 is like a hollow cylinder protruding from the periphery of the cap base 400. The cap wedged section 412 is formed on the cap body 402 with a tapered inner surface. The cap wedged section 412 corresponds to the body tapered section 204. The cap screw thread 410 is formed on a section of the inner surface of the cap body 402, which corresponds to and engages the body threaded section 202 on the lower body part 22. The tube 404 protrudes from the cap base 400 at the center and has a size smaller than the tube holding hole 301 thus allowing the tube 404 to enter the tube holding hole 301. The screw opening 405 through the cap base 400 matches the inner surface of the tube 404. The tapered section 408 is formed on top of the tube 404 with the screw mounting hole 407 defined at its center. The screw mounting hole 407 communicates with the screw opening 405 through the chamber enclosed by the tube 404. The first tail-pawl teeth 416 are formed on the upper surface of the cap base 400. The first tail-pawl teeth 416 are evenly positioned around a circle with a gap between two adjacent ones. The first tail-pawl teeth 416 are correspondingly cooperative with the second tail-pawl teeth 300.

With reference to FIG. 1, the screw 80 comprises a round screw head 800 and a cylindrical screw leg 802. The screw head 800 is smaller than the screw opening 405 but bigger than the screw mounting hole 407. The screw leg 802 is threaded and extends from the screw head 800. In use, the screw leg 802 is inserted through the screw mounting hole 407 and securely screwed on the screw receiving hole 303 for attaching the screw 80 to the spool 30.

Figure 9:
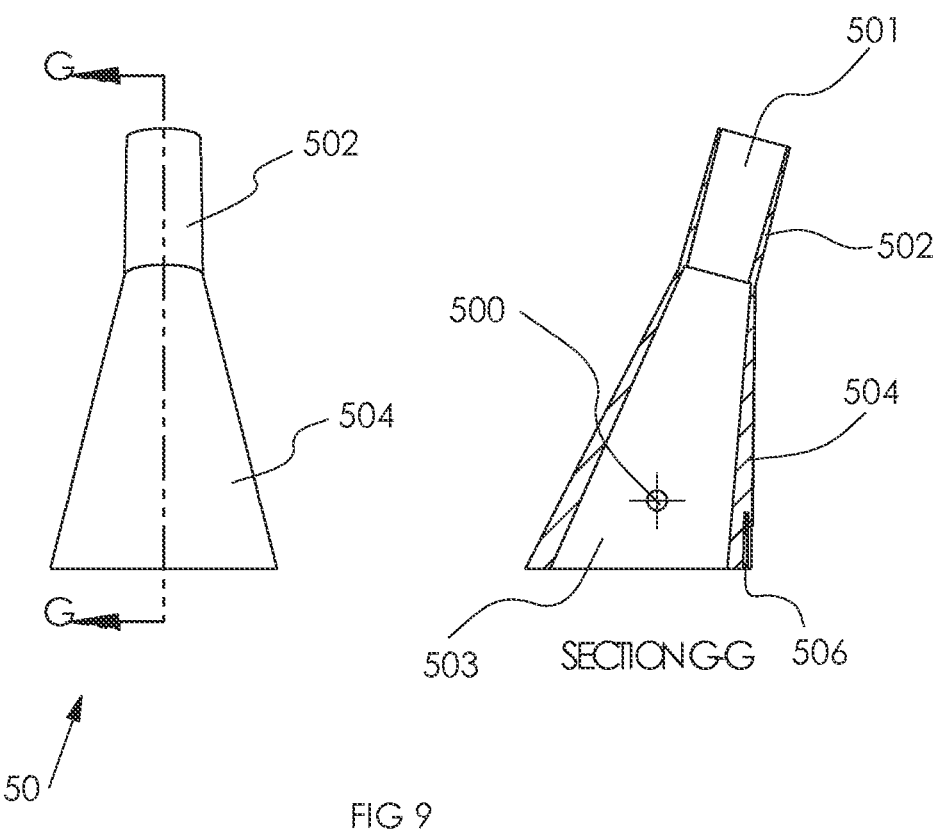
FIG. 9 is a sectional view of a cover of the flossing device, in accordance with some embodiments.

With reference to FIGS. 1, 2 and 9, the cover 50 comprises a lower tapered section 504, an upper tapered section 502, a lower cover chamber 503, an upper cover chamber 501, a cover mounting hole 500, and a cutter notch 506. The lower cover chamber 503 is defined by the lower tapered section 504 and the upper cover chamber 501 is defined by the upper tapered section 502. In assembly, the cover 50 is used to cover the head mounting section 210 and the installation slot 105. The cover mounting hole 500 is defined by the lower tapered section 504 for mounting the cover 50 over the head mounting section 210. A cutter (not shown) is securely mounted in the cutter notch 506 and comprises a blade for cutting dirtied dental floss 306.

In some embodiments, the spring 420 is disposed between the spool 30 and the tail cap 40. For example, in use, the spring 420 is placed on or attached firmly to the cap base 400 around the tube 404 inside the first tail-pawl teeth 416. Then the floss spool 30 is placed on the spring 420. The diameter of the spring 420 is chosen such that the section of the lower surface of the cap head 302, which is between the tube holding hole 301 and the second tail-pawl teeth 300, abuts the spring 420. By contacting only the surface outside the tube holding hole 301, the compression and un-compression of the spring 420 do not interfere with the movement of the tube 404 and the tapered section 408 inside the tube holding hole 301. When not compressed, the spring 420 holds the spool 30 up to a position so that the first tail-pawl teeth 416 do not collide with the second tail-pawl teeth 300 when the spool 30 spins.

In some embodiments, for three purposes, the screw leg 802 is inserted through the screw mounting hole 407 and is partially securely screwed on the screw receiving hole 303 with the screw head 800 disposed inside the tube 404. Firstly, the screw leg 802 together with the spool 30 can be held by the screw mounting hole 407 when the spool 30 is being rotated relative to the housing in both the first and second directions. Secondly, when the tail cap 40 is in the first position, the chamber of the tube 404 provides room for the screw head 800 to move up and down together with the spool 30 for accommodating the engagement between the second body-pawl teeth 312 and the first body-pawl teeth 226. Thirdly, when the tail cap 40 is moving from the first position to the second position, the tapered section 408 engages the screw head 800 to draw the screw 80 together with the spool 30 downwardly for detaching the second body-pawl teeth 312 away from the first body-pawl teeth 226.

The clamping nut 60 is put on the support bar 104 of the head 10. For threading the dental floss 306, the distal end of the dental floss 306 passes sequentially through: (1) the slider guiding groove 209, (2) the hole inside the slider 710 into the chamber between the inner wall 216 and the outer wall 206, (3) the threading opening 220 on the support base 224, (4) the lower cover chamber 503 and the upper cover chamber 501, (5) the threading hole 106 on the head 10, (6) first arm guiding groove 112 on the first arm 110, (7) the second-arm guiding groove 122 on the second arm 120, (8) the threading notch 132, and (9) the fastening notch 138. The distal end of the dental floss 306 is clamped by the clamping nut 60 when it is screwed onto the head thread section 134. This accomplishes the winding work of the dental floss.

To mount the head 10 onto the main body 20, the head 10 is inserted through the upper cover chamber 501 until the top of the cover 50 is aligned with the bottom of the head thread section 134. In the meantime, the assembly hole 100 is aligned with the cover mounting hole 500. In some embodiments, the head 10 is bonded with the upper tapered section 502 through solvent welding to prevent saliva from contaminating the dental floss 306 that is enclosed by the cover 50. The head 10 is then inserted into the head mounting section 210 with the installation slot 105 sliding along the installation rib 234 until the assembly hole 100 is also aligned with the head mounting hole 212. The cover 50 is disposed on top of the support base 224 without blocking the threading opening 220 and the band opening 230. There is a gap formed between the lower tapered section 504 and the head mounting section 210. Such a gap is also connected with the threading hole 106 through the installation slot 105 to allow the dental floss 306 being pulled substantially freely through the lower cover chamber 503 and the threading hole 106. The cover 50, the head mounting section 210, and the head 10 are then fastened together using screws (not shown). Thereafter, the tail cap 40 is screwed onto the body threaded section 202. The assembly work is complete.

Figure 11:
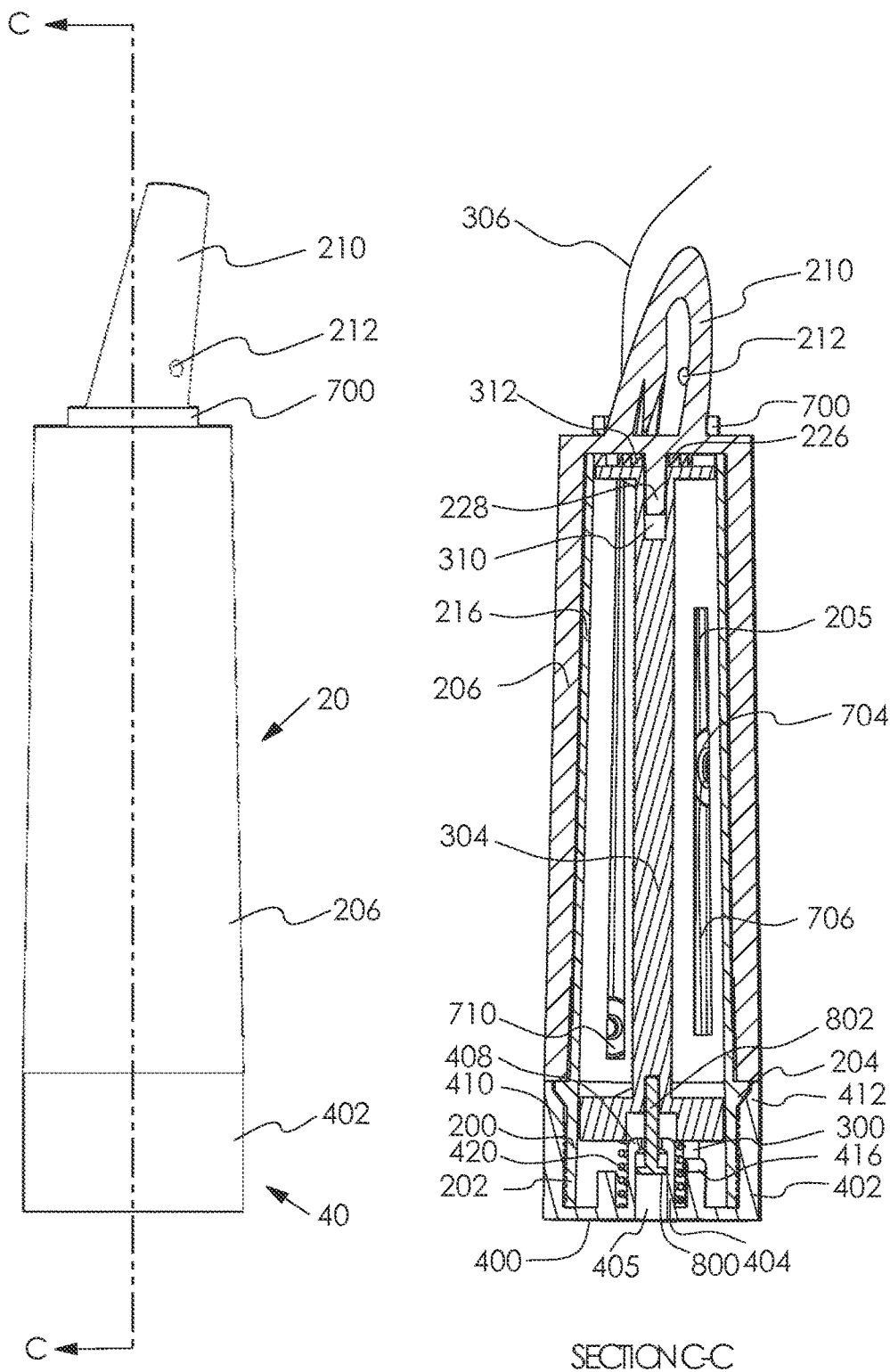
FIG. 11 is an operational perspective view of the flossing device in partial section when floss is being tightened, in accordance with some embodiments.
Figure 12:
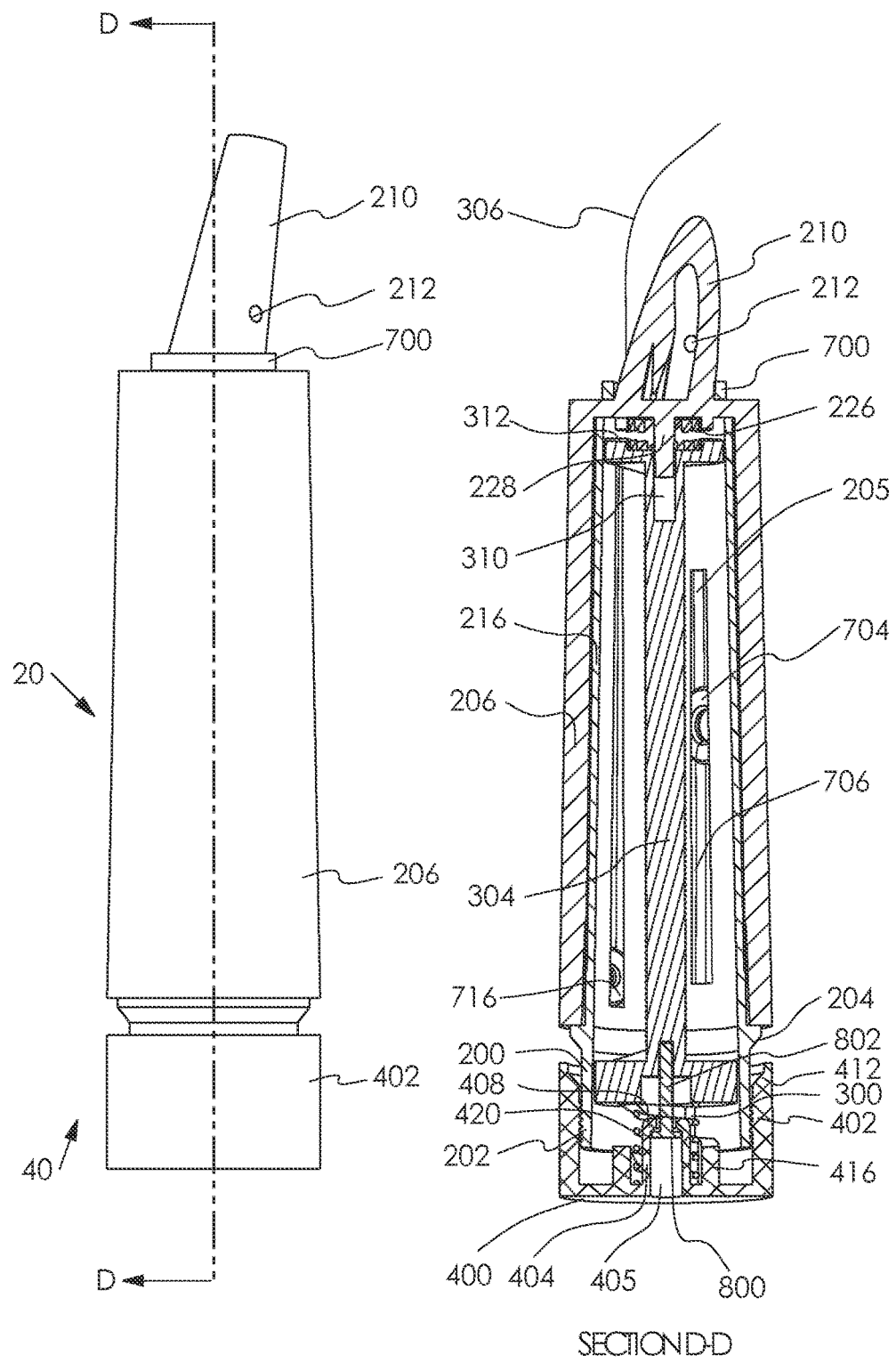
FIG. 12 is an operational perspective view of the flossing device in partial section when floss is being released, in accordance with some embodiments.

As illustrated in FIGS. 11 and 12 and described above, the tail cap 40 is configured to be in one of a plurality of positions including a first position (shown in FIG. 11) and a second position (shown in FIG. 12). As used herein, the first position and second position of the tail cap 40 are positions relative to the housing. In some embodiments, the tail cap 40 is coupled with the housing using a threaded connection.

In some embodiments, the tail cap is capable of rotating freely in the first direction when the tail cap is in the first position (e.g., freely of the threads on the body threaded section 202). Thus, the first position is the position in which the tail cap can be spun by the user to tighten the floss. To reach the first position, the tail cap 40 is screwed onto the body threaded section 202 by rotating it in the tightening direction. As the tail cap is screwed onto the body threaded section 202, the spool 30 is pushed by the spring 420 so that it moves closer to the first body-pawl teeth 226. The tail cap 40 is in the first position when the cap screw thread 410 of the tail cap 40 passes the body threaded section 202 and is disposed at the free rotation section 200. Stated another way, above the threaded section, the housing has a free rotation section allowing the tail cap to rotate relative to the housing without screw engagement (e.g., an un-threaded section or tube with a diameter the same as or slightly smaller than the minor diameter of the threads on the body threaded section 202). Stated yet another way, the tail cap 40 is in the first position when it is screwed toward the housing using the threaded connection.

More specifically, FIG. 11 illustrates the engagement relationship between different parts when the tail cap 40 is in the first position (e.g., the position for tightening the dental floss). When in the first position, compression of the spring 420 exerts a force on the spool to cause engagement of the first set of one or more pawl teeth with the second set of one or more pawl teeth. To that end, the tail cap 40 is screwed onto the body threaded section 202 by rotating it in the tightening direction. The spool 30, being pushed by the spring 420, gets closer to the first body-pawl teeth 226. The sizes of parts are chosen so that, when the tail cap 40 is in the first position, they engage each other in the following manner.

1. The cap wedged section 412 on the tail cap 40 abuts the body tapered section 204 on the main body 20, and the body threaded section 202 reaches the cap base 400 on the tail cap 40. As a result, the tail cap 40 is prevented from moving up. Since the cap screw thread 410 can rotate over the free rotation section 200 and the body threaded section 202 holds the cap screw thread 410 to prevent the tail cap 40 from dropping off the main body 20, the tail cap 40 can continue being rotated in the tightening direction.
2. The spring 420 is compressed resulting in the stop faces of first tail-pawl teeth 416 on the tail cap 40 partially contacting the stop faces of the second tail-pawl teeth 300 for driving the spool 30.
3. Compression of the spring 420 exerts a longitudinal upward force on the spool 30 to cause engagement of the second body-pawl teeth 312 with the first body-pawl teeth 226.

To add tension to (i.e., tighten) the dental floss, the tail cap 40 is turned in the tightening direction. The first tail-pawl teeth 416 urge the second tail-pawl teeth 300 to rotate also in the tightening direction. When the second body-pawl teeth 312 engage the first body-pawl teeth 226 through the spring 420, the spool 30 and the screw 80 move up and down, which is made possible by letting the stop faces of the second tail-pawl teeth 300 on the spool 30 move along the stop faces of the first tail-pawl teeth 416 and letting the screw head 800 move inside the chamber of the tube 404. As a result, the deflection faces of the second body-pawl teeth 312 on the spool 30 are able to glide over the deflection faces of the first body-pawl teeth 226 by compressing the spring 420, which enables the spool 30 to spin in the tightening direction. Meantime, the stop faces of the first body-pawl teeth 226 block the stop faces of the second body-pawl teeth 312 on the spool 30 due to the force exerted by the compressed spring 420 on the spool 30. This prevents the spool 30 from spinning reversely. As a result, turning the tail cap 40 in the tightening direction rotates the spool 30 in the tightening direction only. If the distal end of the dental floss 306 is not fastened, rotating the spool 30 in the tightening direction winds the floss 306 back on the spool. If the distal end is clamped by the clamping nut 60, the distal end of the floss 306 is pulled so that the length of floss suspended by the fork is tightened.

The tail cap 40 is put in the second position when it moves down the housing using the threaded connection beyond a mechanical threshold that disengages the second body-pawl teeth 312 from the first body-pawl teeth 226 and the first tail-pawl teeth 416 from the second tail-pawl teeth 300. Stated another way, in the second position, the spring does not cause restrictive engagement of the first set of one or more pawl teeth with the second set of one or more pawl teeth. In some embodiments, when the tail cap 40 is in the second position, the spool 30 is rotatable in the second direction (e.g., opposite the first direction) and the length of floss suspended by the fork is loosened or dispensed. In this manner, the length of floss is replaced across the fork with a fresh length of floss by the user pulling on the free end of the floss 306 with the tail cap 40 in the second position, thereby dispensing the fresh length of floss from the spool.

FIG. 12 illustrates the engagement relationship between different parts when the tail cap 40 is put in the second position for releasing the dental floss 306. In order to switch the tail cap 40 from the first position to the second position, the user turns the tail cap 40 in the unscrewing (second) direction relative to the main body 20 via the engagement between the cap screw thread 410 and the body threaded section 202. Because the first body-pawl teeth 226 on the main body 20 are initially engaging the second body-pawl teeth 312 on the spool 30 by the stop faces, the spool 30 remains still. Because of the gaps between two adjacent first tail-pawl teeth 416 and two adjacent second tail-pawl teeth 300, the deflection faces of the first tail-pawl teeth 416 can glide over the deflection faces of the second tail-pawl teeth 300 without collision. Stated another way, the tail cap 40 can be unscrewed from the main body 20 without the first tail-pawl teeth 416 colliding with the second tail-pawl teeth 300.

The following are representative dimensions provided in accordance with a variety of embodiments. The pitch of the cap screw thread 410 and the screw thread on the body threaded section 202 is 6 millimeters. There are two first tail-pawl teeth 416 and second tail-pawl teeth 300 with each spanning 90 degrees around a circle. The height of the first tail-pawl teeth 416 and the second tail-pawl teeth 300 increases linearly from 0 to 6 millimeters with the angle. Therefore, the height of the stop faces of the first tail-pawl teeth 416 and the second tail-pawl teeth 300 is 6 millimeters and the gaps between two adjacent first tail-pawl teeth 416 and two adjacent second tail-pawl teeth 300 span 90 degrees. The height of the second body-pawl teeth 312 and the first body-pawl teeth 226 is 2.5 millimeters. In the first position, when the first tail-pawl teeth 416 and the second tail-pawl teeth 300 are engaged to tighten the floss 306, the height of the section by which they contact each other is 2.8 millimeters. The remaining 3.2 millimeters of the stop faces of the first tail-pawl teeth 416 are reserved for the stop faces of the second tail-pawl teeth 300 moving down to accommodate the second body-pawl teeth 312 gliding over the first body-pawl teeth 226 by the compression and uncompression of the spring 420. With these configurations, when the tail cap 40 is rotated half round in the unscrewing direction via the thread connection, the pitch of the cap screw thread 410 and the body threaded section 202 of 6 millimeters determines the tail cap 40 and also the first tail-pawl teeth 416 descend 3 millimeters, which is bigger than the height of the contact section of 2.8 millimeters between the first tail-pawl teeth 416 and the second tail-pawl teeth 300 and therefore collision is avoided.

When the tail cap 40 spirals downwardly along the main body 20, the tapered section 408 engages the screw head 800 to pull it together with the spool 30 downwardly causing the second body-pawl teeth 312 to disengage from the first body-pawl teeth 226. Without pressing force from above, the spring 420 bounces back and pushes the spool 30 upwardly causing the second tail-pawl teeth 300 to disengage from the first tail-pawl teeth 416. Since one end of the spool 30 is held by the axle 228 through the main-body holding hole 310 and the other end is held by the screw mounting hole 407 via the screw leg 802, the spool 30 spins to release the dental floss 306 when its distal end is being pulled.

To facilitate the spinning of the spool 30, the direction of pulling force needs to be made more perpendicular to the reel 304. For this purpose, the dental floss 306 received from the spool 30 goes through the hole of the slider 710. When the distal end of the dental floss 306 is being pulled, an upward pulling force is exerted on the slider 710, which is propagated through the cable 706 to pull the moving block 704 downward by extending the elastic band 702. At the same time, the extended elastic band 702 also exerts a downward force on the slider 710 through the cable 706. Because the dental floss 306 goes through the hole of the slider 710, the direction of pulling force exerted on the spool 30 from the dental floss 306 changes according to the position of the slider 710. In addition, the strength of pulling force exerted on the spool 30 from the dental floss 306 is reduced when the spool 30 spins to release the dental floss 306. As a result, the slider 710 moves up along the slider guiding groove 209 to a position where the upward force from the dental floss 306 and the downward force from the elastic band 702 are balanced and the spool 30 can be rotated for releasing the dental floss 306. When the free end of the dental floss 306 is not being pulled, the elastic band 702 retracts and pulls the slider 710 to the bottom of the slider guiding groove 209.

To remove used dental floss, the distal end of the dental floss 306 is freed by unscrewing the clamping nut 60 from the head thread section 134. The dirty dental floss suspended by the fork can be cut away. The head 10 can be washed clean under tap water. In some embodiments, after the dental floss 306 is depleted, floss can be refilled by replacing a new spool cartridge wound with new dental floss.

The flossing device as described can (1) clamp the distal end of the dental floss 306 through the clamping nut 60 and the head thread section 134, and (2) tighten or retract the dental floss 306 by rotating the tail cap 40 in the tightening direction, and (3) release the dental floss 306 by rotating the tail cap 40 in the unscrewing direction, and then pulling the distal end, and (4) remove the dirtied floss 306 immediately after use, (5) be reused while the dental floss 306 can be refilled. As a result, the user's teeth can be flossed conveniently.

In some embodiments, the spool 30 holds dental floss. In some embodiments, the spool 30 is reloadable by the user by either replacing a new spool wrapped with new dental floss or wrapping new floss around the old spool. In some embodiments, the floss is not directly wound onto the spool, but is wound onto a replaceable spool cartridge that is coupled with the spool, which fits snuggly and/or tightly over the spool 30 (that is to say, when the spool 30 is rotated as described herein, the spool cartridge rotates together with the spool 30). In some embodiments, the spool is not reloadable by the user. The flossing device is disposed once a pre-loaded amount of dental floss has been used.

In an alternative embodiment, other types of strings other than dental floss including but not limited to guitar strings and fishing line can be tightened and released using the mechanism disclosed.

In an alternative embodiment, the tail cap 40 and main body 20 are not coupled by thread connection. Instead, an elastic part is mounted on the outer surface of the main body 20 and a protrusion is formed on the inner surface of the tail cap 40. With the elastic part and protrusion, the tail cap 40 is clipped on the main body 20 when being pushed and detaches from the main body 20 when being pulled. When the tail cap 40 is clipped on the main body 20, it is in the first position at which the first tail-pawl teeth 416 engage the second tail-pawl teeth 300 for tightening the dental floss 306. When the tail cap 40 is detached from the main body 20, it is at the second position, at which the first tail-pawl teeth 416 become disengaged from the second tail-pawl teeth 300 for releasing the dental floss 306. Alternatively, an elastic part is mounted on the tail cap 40 and a protrusion is formed on the main body 20.

In an alternative embodiment, the axle 228 is removed from the main body 20 and a through hole is defined by the spool 30 at the center. Without the tube 404, an elongated shaft protrudes from the cap base 400. Alternatively, an arc shaped hook is mounted at the center of the cap base 400 and an elongated shaft is connected to the hook. In both cases, the shaft goes through the through hole to support and act as an axle for the spool 30. An enlarged disc is mounted at the end of the shaft for dragging the spool 30 when the tail cap 40 is being switched from the first position to the second position.

In an alternative embodiment, the main body 20, the spool 30, the spring 420, and the tail cap 40 are positioned horizontally instead of vertically. In such embodiments, the user holds the main body 20 in her palm for flossing.

In an alternative embodiment, an opening defined on the inner wall 216 at a fixed position is used for leading the dental floss 306 out of the hollow interior of the housing.

In an alternative embodiment, a movable slider having a hole, wherein floss is threaded through the hole such that, when an end of the floss is pulled to release additional floss from the spool 30, the floss exerts a first force on the movable slider in a first direction substantially along an axis of the spool and an elastic object coupled with the movable slider (either via a cable or being directly connected to) that exerts a second force on the movable slider in an opposite direction to the first direction when the elastic object is stretched.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Although some of the various drawings illustrate a number of logical stages in a particular order, stages that are not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software or any combination thereof.

The foregoing description, for purpose of explanation, has been described with reference to specific embodiments.

However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A flossing device, comprising:
   a housing forming a handle of the flossing device and having a cap portion and a pawl teeth portion opposite the cap portion along an axis of rotation, wherein the housing has a hollow interior with a first set of one or more pawl teeth disposed within the hollow interior around the axis of rotation adjacent the pawl teeth portion of the housing;
   a spool, disposed along the axis of rotation within the hollow interior of the housing, for holding floss, wherein the spool includes a second set of one or more pawl teeth disposed on a first end of the spool around the axis of rotation and a third set of one or more pawl teeth disposed on a second end of the spool opposite the first end of the spool around the axis of rotation, wherein the second set of one or more pawl teeth, when engaged with the first set of one or more pawl teeth, allows the spool to rotate in a first direction relative to the housing;
   a tail cap disposed adjacent the cap portion of the housing that includes a fourth set of one or more pawl teeth around the axis of rotation that engages the third set of one or more pawl teeth disposed on the second end of the spool to urge the spool in the first direction; and
   a fork for suspending a length of floss received from the spool, wherein the length of floss is used for flossing by a user of the flossing device, and the length of floss is tightened by rotation of the spool in the first direction.

2. The flossing device of claim 1, further include a spring disposed between the spool and the tail cap.

3. The flossing device of claim 2, wherein the tail cap is configured to be positioned in a plurality of positions including a first position wherein compression of the spring exerts a force on the spool to cause engagement of the first set of one or more pawl teeth with the second set of one or more pawl teeth and a second position wherein the spring does not cause restrictive engagement of the first set of one or more pawl teeth with the second set of one or more pawl teeth.

4. The flossing device of claim 3, wherein the fourth set of one or more pawl teeth drives the third set of one or more pawl teeth when the tail cap is in the first position.

5. The flossing device of claim 3, wherein the fourth set of one or more pawl teeth disengages with the third set of one or more pawl teeth when the tail cap is in the second position.

6. The flossing device of claim 3, wherein the tail cap is mechanically coupled with the spool such that the second set of one or more pawl teeth is disengaged from the first set of one or more pawl teeth when the tail cap is in the second position.

7. The flossing device of claim 3, wherein, when the tail cap is in the second position, the spool is rotatable in a second direction opposite the first direction, wherein the length of floss is loosened or dispensed by rotation of the spool in the second direction.

8. The flossing device of claim 3, wherein the tail cap is coupled with the housing using a threaded connection, and wherein the tail cap is in the first position when the tail cap is screwed toward the housing using the threaded connection and the tail cap is in the second position when the tail cap is loosened using the threaded connection beyond a mechanical threshold that disengages the second set of one or more pawl teeth from the first set of one or more pawl teeth.

9. The flossing device of claim 8, wherein the tail cap is capable of rotating freely in the first direction when the tail cap is in the first position.

10. The flossing device of claim 8, wherein the length of floss is replaced across the fork with a fresh length of floss by the user pulling on the floss with the tail cap in the second position, thereby dispensing the fresh length of floss from the spool.

11. The flossing device of claim 1, wherein the housing includes an assembly of separately manufactured components.

12. The flossing device of claim 1, further including a releasable clamp for clamping a loose end of the floss in order to maintain tension in the length of floss suspended by the fork.

13. A flossing device, comprising:
    a housing forming a handle of the flossing device, wherein the housing has a hollow interior with a first set of one or more pawl teeth disposed within the hollow interior;
    a spool, disposed within the hollow interior of the housing, for holding floss, wherein the spool includes a second set of one or more pawl teeth disposed on a first end of the spool and a third set of one or more pawl teeth disposed on a second end of the spool opposite the first end of the spool, wherein the second set of one or more pawl teeth, when engaged with the first set of one or more pawl teeth, allows the spool to rotate in a first direction relative to the housing;
    a tail cap that includes a fourth set of one or more pawl teeth that engages the third set of one or more pawl teeth to urge the spool in the first direction;
    a fork for suspending a length of floss received from the spool, wherein the length of floss is used for flossing by a user of the flossing device, and the length of floss is tightened by rotation of the spool in the first direction;
    a releasable clamp for clamping a loose end of the floss in order to maintain tension in the length of floss suspended by the fork; and
    a support bar coupling the fork with the housing, wherein:
    the support bar includes a thread; and
    the releasable clamp includes a screw nut positioned around the support bar to be tightened against the thread.

14. The flossing device of claim 1, wherein the flossing device is a reusable handheld flossing device.

15. The flossing device of claim 1, wherein the spool is reloadable by the user.

16. The flossing device of claim 1, wherein the spool is not reloadable by the user.

17. A flossing device, comprising:
    a housing forming a handle of the flossing device, wherein the housing has a hollow interior with a first set of one or more pawl teeth disposed within the hollow interior;
    a spool, disposed within the hollow interior of the housing, for holding floss, wherein the spool includes a second set of one or more pawl teeth disposed on a first end of the spool and a third set of one or more pawl teeth disposed on a second end of the spool opposite the first end of the spool, wherein the second set of one or more pawl teeth, when engaged with the first set of one or more pawl teeth, allows the spool to rotate in a first direction relative to the housing;

a tail cap that includes a fourth set of one or more pawl teeth that engages the third set of one or more pawl teeth to urge the spool in the first direction;

a fork for suspending a length of floss received from the spool, wherein the length of floss is used for flossing by a user of the flossing device, and the length of floss is tightened by rotation of the spool in the first direction; and an apparatus for dispensing the floss from the spool, the apparatus comprising:

a movable slider having a hole, wherein the floss is threaded through the hole such that, when an end of the floss is pulled to release additional floss from the spool, the floss exerts a first force on the movable slider in a first direction substantially along an axis of the spool; and an elastic object coupled with the movable slider that exerts a second force on the movable slider in an opposite direction to the first direction when the elastic object is stretched.

18. The flossing device of claim 17, wherein the apparatus further includes:

a moving block coupled with the elastic object, wherein the moving block is displaced by changes in a tension of the elastic object;

a cable coupled with the moving block and the moveable slider; and a fixed block that is fixed in position with respect to the spool, wherein the fixed block has a plurality of threading holes through which to thread the cable;

wherein the cable is threaded through the plurality of threading holes of the fixed block so as to change the direction of the cable.

* * * * *